United States Patent [19]
Siebert

[11] 4,043,185
[45] Aug. 23, 1977

[54] DEVICE FOR NON-DESTRUCTIVE TESTING OF ROLLED STEEL PLATE AND THE LIKE

[75] Inventor: Hans-Werner Siebert, Oxelosund, Sweden

[73] Assignee: Granges Oxelosunds Jarnverk AB, Sweden

[21] Appl. No.: 658,100

[22] Filed: Feb. 13, 1976

[30] Foreign Application Priority Data
Feb. 13, 1975 Germany .................. 2506072

[51] Int. Cl.² .......................................... G01N 29/04
[52] U.S. Cl. .................................................. 73/67.7
[58] Field of Search .............. 73/67.7, 67.8 R, 67.8 S, 73/67.9, 71.5 US, 67.5 R; 324/37, 40

[56] References Cited
U.S. PATENT DOCUMENTS

| 3,188,859 | 6/1965 | Greenberg et al. | 73/71.5 US |
| 3,257,843 | 6/1966 | Cowan | 73/71.5 US |
| 3,553,570 | 1/1971 | Skubiak et al. | 73/67.8 S |
| 3,628,374 | 12/1971 | Laudien et al. | 73/67.8 S |
| 3,872,378 | 3/1975 | Shiraiwa et al. | 73/67.8 S |

FOREIGN PATENT DOCUMENTS
704,450  2/1965  Canada ................... 73/71.5 US

Primary Examiner—Richard C. Queisser
Assistant Examiner—Stephen A. Kreitman
Attorney, Agent, or Firm—Craig & Antonelli

[57] ABSTRACT

A device for the non-destructive testing of rolled steel plate and the like for the presence of internal flaws or defects such as non-metallic inclusions, inhomogeneities and the like, comprising a carriage adapted to be traversed in relation to the surface of the plate to be tested and parallel thereto, said carriage having attached thereto, through the medium of connecting links, at least one ultrasonic test head including an ultrasonic transmitter and an ultrasonic receiver supported by a test head holder and adapted to be tilted about two mutually perpendicular tilting axes extending substantially parallel to the surface of the plate to be tested, said connecting links being adapted to raise and lower said test head holders individually and comprising for each test head holder both an elevating cylinder and separate guide means adapted positively to guide said test head holder in a direction extending at right angles to the raising and lowering direction, said elevating cylinder and said guide means being coupled to said test head holder through the medium of pivotal joints having a common rotational axis constituting one of said two tilting axes of said test head holder.

23 Claims, 9 Drawing Figures

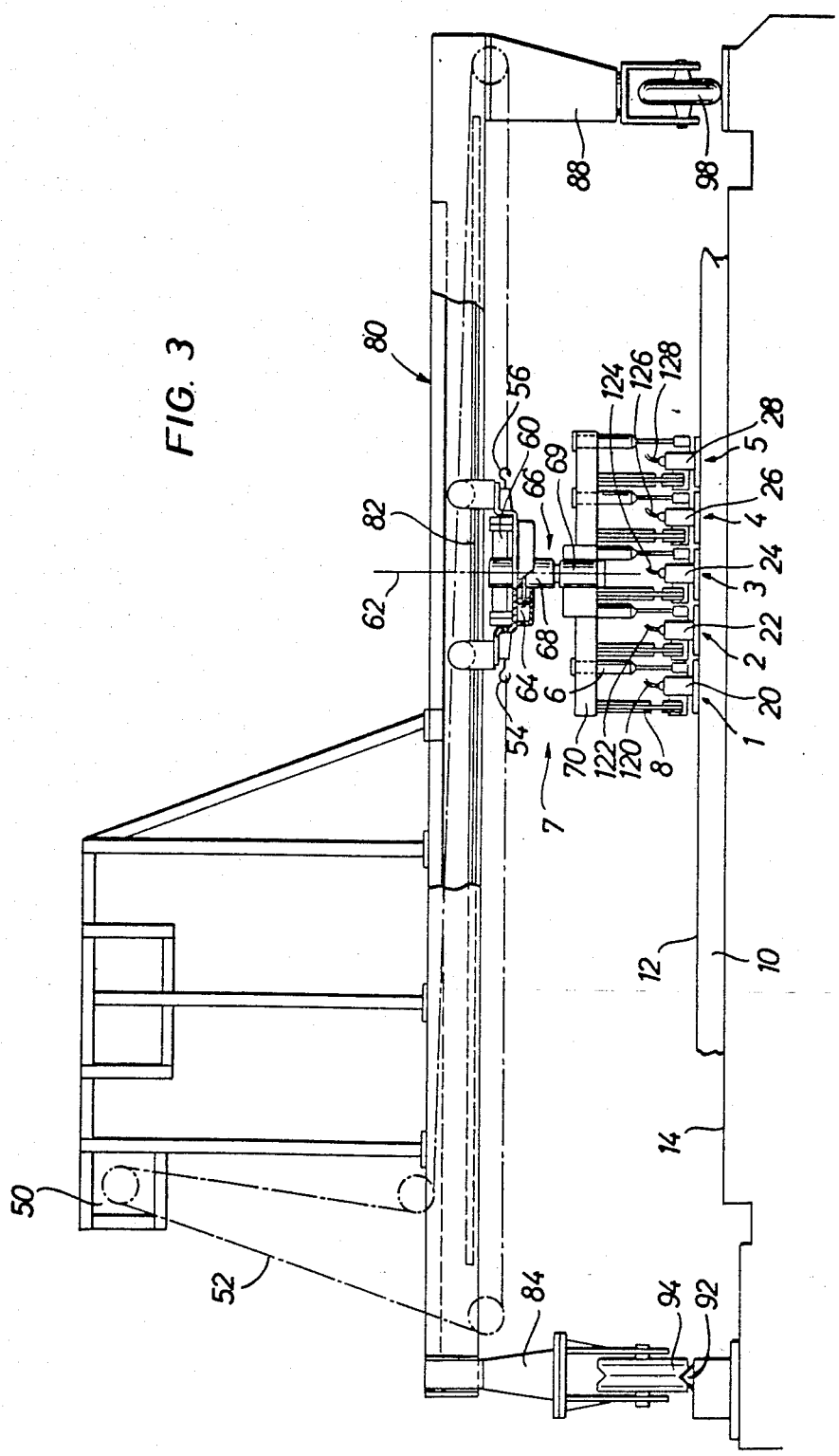

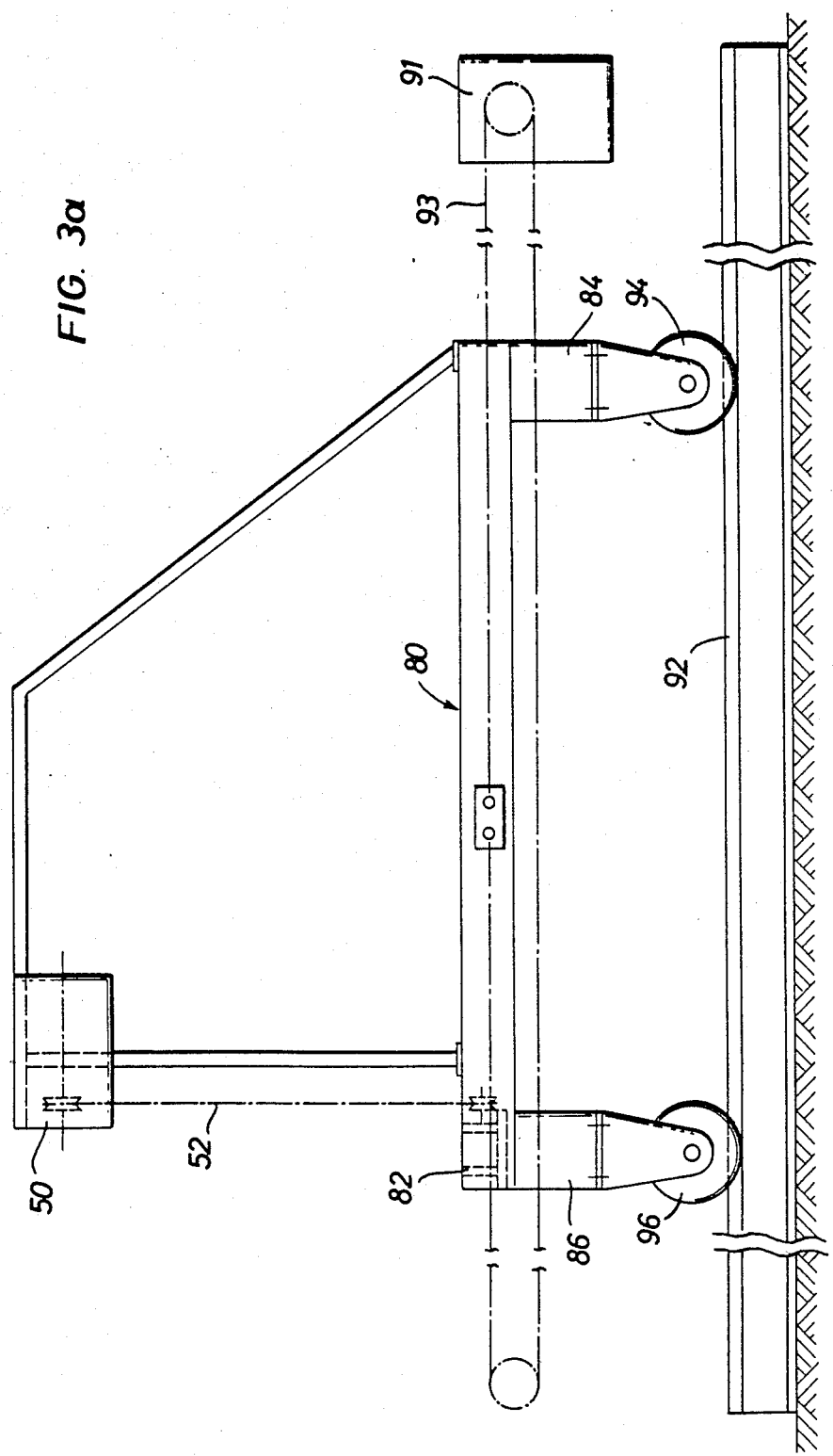

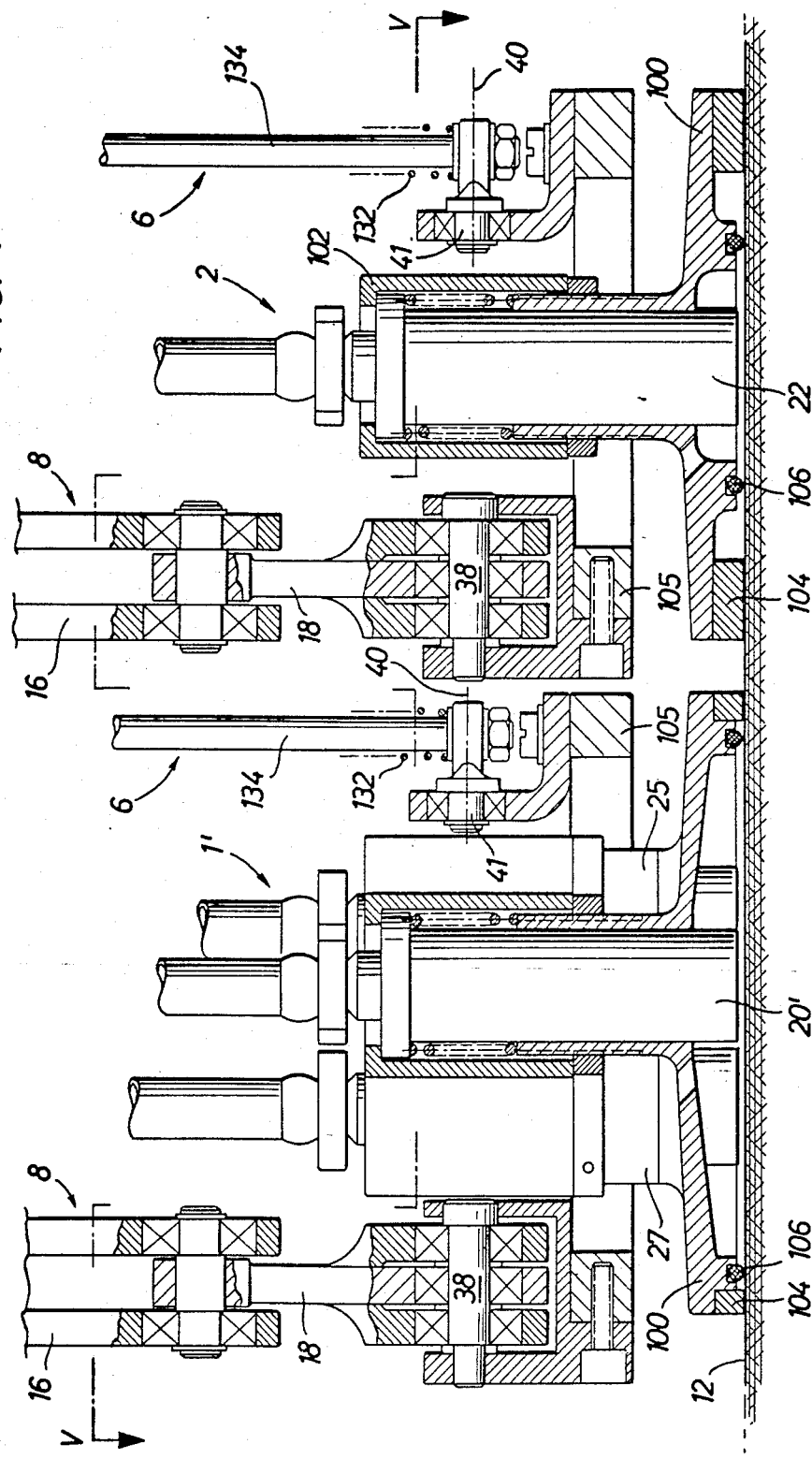

DEVICE FOR NON-DESTRUCTIVE TESTING OF ROLLED STEEL PLATE AND THE LIKE

This invention relates to a device for non-destructive testing of rolled steel plate and the like for the purpose of detecting hidden or internal flaws such as non-metallic inclusions, discontinuities and the like, such device comprising a guiding means or carriage means adapted to be moved in relation to the plate under test and parallel to the surface thereof, said guiding or carriage means supporting, through the medium of intermediate links, at least one ultrasonic test head comprising an ultrasonic generator and detector unit carried by support means associated therewith, the said intermediate links being adapted to permit the or each test head support means to be separately adjusted vertically in relation to the surface of the plate under test.

In many cases it is either desirable or required that rolled steel plate, particularly heavy-gauge plate, be tested for the presence of hidden or internal non-metallic inclusions, blowholes and other discontinuities. For the purpose of detecting such defects, it has been known to test the plate material with the aid of ultrasonic energy. For this purpose, it has been conventional to employ an ultrasonic transmitter which is brought into contact with the surface of the plate under test through a contacting medium, preferably water, such transmitter being adapted to introduce ultrasonic pulses into the plate, such pulses producing reflected pulses from the characteristics of which conclusions may be drawn as regards defects possibly present within the plate. It should be understood in this connection that such flaws will produce, in addition to the reflexions caused by the upper and lower surfaces of the plate, characteristic reflexions which are capable of being detected. Hitherto it has been conventional to employ a manually operable carriage supporting at least one test head comprising an ultrasonic transmitter and an ultrasonic receiver or a plurality of such test heads spaced along a common line and to move such carriage over the plate surface, said carriage supporting a flaw indicator adapted to indicate the flaws past which the test heads are being moved by means of the carriage. The location of the flaws thus detected is then marked on the surface of the plate either by hand or by means of a manually operable marking means associated with the underside of the carriage, both the location and the size of the flaws being noted in a test record.

However, the use of such known testing devices is extremely time-consuming and is very tiring for the operators who have to move the carriage over the plate. Moreover, it is extremely difficult, when using such testing devices, to provide for the device to be moved over the plate under test accurately in a predetermined direction or in accordance with a predetermined pattern, particularly in cases in which the plate under test exhibits surface irregularities such as ripples or corrugations extending in a transverse or longitudinal or diagonal direction. It should be understood in this connection that it is of extreme importance for the reliability of the test to provide for close adherence to predetermined tracing directions or tracing patterns in order to ensure compliance with test specifications or customer's specifications which may call for predetermined plate portions to be tested in a reliable manner.

It is a primary object of the present invention to provide an improved device for the non-destructive testing of rolled steel plate and the like wherein the test heads are adapted to be brought into contact with the surface of a plate under test and to be moved in relation thereto along paths the location of which is predetermined with the greatest possible accuracy.

According to the invention, this object is attained by the provision of a device of the aforesaid type in which the said intermediate links supporting the or each test head support from said guiding means or a carriage comprise, in association with each test head support and in addition to reciprocating means preferably comprising a single ram cylinder, separate guiding means adapted positively to guide said test head support in a direction extending at right angles to the upward and downward reciprocation thereof.

The device of the invention affords the advantage that said ram cylinders are completely relieved of guiding forces, that only a single ram cylinder need be associated with each test head support, and that the test heads may be forced with sufficient force against the plate surface in order to prevent excessive amounts of coupling fluid from escaping, this being achieved without the increased frictional forces produced thereby presenting any problems regarding the accurate guidance of the test heads.

According to the invention it is preferred to provide for each test head to be pivotable about at least one axis extending substantially at right angles to the tracing direction and substantially parallel to the plate surface so as to enable the test head to conform at least to the surface waves or corrugations occurring in the tracing direction. It is particularly preferred, according to the invention, to provide for each test head to be additionally pivotable about a second axis extending substantially parallel to the tracing direction and substantially parallel to the plate surface so as to enable the test head substantially to conform to all surface irregularities of the plate and to remain in constant contact with the plate surface.

According to the invention, there cooperate with each test head at least one guiding member and at least one elevating member of variable length, each of such members being engaged at one end thereof with said guiding means and at the other end thereof with said test head and being adapted substantially independently of one another to transmit guiding forces and reciprocating forces, respectively, to their associated test heads.

The guiding members are preferably constructed as toggle lever arrangements each comprising two oppositely deflectable struts which are interconnected at at least one pair of adjacent ends thereof by means of interengaging gear wheels so as to provide for substantially accurate guidance of the test heads in a direction perpendicular to the surface of the plate under test.

The said elevating arrangements are preferably constructed as single-acting pneumatic or hydraulic cylinders adapted to raise the test heads which preferably are held in contact with the plate surface by gravity, as soon as the test heads assume a position externally of the surface area under test upon the test being completed.

In view of the fact that the dead weight of the test heads and thus the contact pressure between the test heads on the one hand and the plate surface on the other may become very great in cases in which use is made of large and heavy test heads, it may be possible, in order to reduce sliding friction, to provide for the or each elevating arrangement to be operable in an upward direction in such a manner as to compensate for part of the dead weight of the or each test head and to cause the or each test head to be forced against the plate surface by a predetermined force which is smaller than the said dead weight. Such counterbalancing means may also be provided in the form of counterweights or compensating springs.

It may also be of advantage to construct the said elevating arrangements in the form of double-acting pneumatic or hydraulic cylinders so as to permit the test heads to be urged against the plate surface by a predetermined force. This will be necessary in such cases, in particular, in which the dead weight of the test heads does not suffice to move them from their elevated positions into contact with the plate surface and to maintain them in contact therewith in the absence of an additional external force.

According to the invention it is possible to provide for positive guidance of the test heads in the tracing direction, i.e. without any lateral deviation from the tracing direction, by providing for the guiding members to have one end thereof to be attached to the guiding means and their other end to the upper portion of the associated test head through the medium of pivotal joints the axes of which extend substantially at right angles to the tracing direction of the test heads and substantially parallel to the plate surface, the pivot axis of the joint provided on the upper portion of the test head coinciding with the aforementioned first pivot axis of the test head.

According to the invention, the guide means comprise a travelling supporting structure adapted to be moved past a testing station at which the plates under test are to be located, the said supporting structure comprising at least one transverse beam extending substantially at right angles to the tracing direction and over the entire plate area to be tested, the said supporting structure further being formed as a track adapted to cooperate with a wheeled carriage having at least three wheels and adapted to support the test heads, at least two wheels being spaced apart in the tracing direction and adapted to cooperate with a guiding rail extending the length of said testing station. Whereas the direction of travel of said supporting structure determined by the said guiding rail determines a first direction of motion of the test heads, the direction of travel of said carriage is determined by its cooperation with said transverse beam forming a guiding rail for said carriage determines a second direction of travel of the test heads.

Preferably, there are provided a first drive means adapted to move the said supporting structure along its associated guiding rail, and a second drive means adapted to move said carriage along said transverse beam or second guiding rail. In a preferred embodiment the two drive means are electric motors, preferably electrically operable stepping motors or servo motors permitting, during use of the device, to record the distances travelled by said supporting structure along its guide rail and/or by said carriage along said transverse beam, thus making it possible, if the starting position of the test heads at the commencement of the test is known, to determine the location of detrimental flaws in a plate under test in relation to the said starting position. For the purpose of recording the distances travelled and of thus locating the flaws, it may also be convenient to provide the supporting structure and/or the carriage with a measuring wheel and associated measuring means including a pulse generator, the arrangement being such that the measuring wheel is guided by the guide rail or the guiding means, respectively, constituted by the transverse beam of the supporting structure, the number of the pulses generated by the pulse generator for each full revolution of the measuring wheel bearing a predetermined preferably integral, relation to the distance travelled by the measuring wheel, the result being that it is possible, by counting the pulses generated, to determine the distances respectively travelled by the supporting structure and the carriage and thus by the test heads in relation to the plate surface.

According to the invention, the test heads, which are arranged in side-by-side relationship along a common line, are individually supported by a supporting arm which is adapted to be pivoted about an axis extending perpendicularly to the plate surface, which is carried by said carriage, which extends substantially parallel to the plate surface, and which is vertically adjustable in relation thereto, the lateral distance between strip-like areas to be traced by any two adjacent test heads being substantially equal to a tracing width dimension or an integral multiple of such dimension which is in turn determined by testing elements or probes contained in the test heads.

In order to permit substantially all portions of the plate surface to be traced, the supporting arm carrying the test heads may be arranged to be displaced laterally by 1, 2, 3 or any other integral number of tracing width dimensions, the plate surface being traced by moving the test heads either always in the same direction or in opposite directions in relation to the plate. It may also be convenient to arrange for the supporting arm to be pivoted through an angle of 90° upon one end or edge of the plate or of the predetermined surface area to be tested being reached, thus making it possible to trace the plate at right angles to the previous direction of tracing.

According to another feature of the invention, the testing elements or probes and/or test heads may be disposed in such a manner and/or may be connectible in such a way that predetermined first areas of a plate under test may be subjected to a precision test whereas predetermined second areas of a plate may be subjected to a less stringent test; in such a case, those test heads which are supported by that end of the supporting arm which is arranged to face those areas of the plate which, after the plate has been cut to the desired final dimensions, will constitute the marginal areas to be subjected to a precision test, are so arranged that the spaces between the strip-like areas traced by adjacent test heads are substantially equal to or smaller than the width of a strip-like area traced by a single probe, whereas those test heads which are positioned on that portion of the supporting arm which faces a marginal area to be subjected to a less stringent test are distributed in such a manner that the spaces between the strip-like areas traced by adjacent test heads correspond to an integral multiple of the width of a strip-like area traced by a single probe.

Such-problem-oriented testing of rolled steel plate and the like is necessary in view of the fact that it is just in the said marginal areas that flaws will give rise to the formation of cracks, particularly so in cases in which welding operations have to be performed in such marginal areas. For this reason, it is necessary to subject such marginal areas to precision tests, whilst as far as the areas located within such marginal areas are concerned, it will suffice, in general, to test them in a less stringent manner.

It may also be convenient to substitute for a group or set of test heads at least one test head comprising two or more probes which are spaced from the tracing direction at right angles thereto by an amount corresponding to the tracing width determined by said probes, and to arrange for such test heads to be operable according to changing requirements. Preferably, a test head of such design is mounted on that end of the said supporting arm which faces a marginal area of a plate which is to be subjected to a precision test.

It has also been found to be convenient to provide for detachable mounting of said supporting arm including the test heads mounted thereon in order to permit quick and easy changing of test heads in cases in which plates of different thickness require the use of probes of different capacity or in which it is intended to employ test heads having two or more probes. It may also be convenient to arrange individual probes or sets of probes in an insert adapted to be introduced into a test head so as to eliminate the necessity of exchanging all or the test heads carried by the supporting arm.

In order to permit the lateral spacing of the strip-like tracing areas to be varied it may also be convenient to arrange the test heads on the supporting arm in such a manner as to be movable longitudinally thereof.

According to another preferred feature of the invention, the said supporting arm is connected to said carriage by means of a supporting tube extending at right angles to the plate surface and comprising two separable members which are arranged in telescoping relationship and adapted to be clamped together with the aid of known clamping elements; preferably, the upper tube member is supported for rotation about its longitudinal axis in a bearing provided on the underside of the carriage, the lower tube member being rigidly attached to the supporting arm, with the said clamping elements permitting coarse adjustment of the spacing of the supporting arm from the plate surface to be effected.

According to the invention, each test head comprises at least one probe including an ultrasonic transmitter and an ultrasonic receiver arranged in a probe holder for a vertical adjustment in relation to the plate surface; preferably, there is associated with each probe a spring disposed between the upper end face of the probe holder and an annular shoulder provided at the upper end of the probe, such spring having the function of urging the probe against a downwardly directed annular surface of an internally directed flange formed on the upper end of a substantially cylindrical socket which is in threaded engagement with the probe holder so as to permit the probe holder to be adjusted along its longitudinal axis for the purpose of adjusting the width of the gap between the ultrasound emitting and receiving surface of the probe and the plate surface, said gap influencing the transmission of ultrasonic energy.

Preferably, the upper portion of the probe holder is provided with a bore adapted to introduce, into a zone surrounding the ultrasound emitting and receiving surface of the probe, a suitable coupling medium, the said zone being defined by a sealing ring, preferably an O-ring, which is mounted in an annular groove formed in the underside of the probe holder and which is adapted substantially to prevent the escaping, from the said zone, of the coupling medium introduced through said bore.

In a preferred embodiment, each probe holder is supported from the surface of the plate under test by a plurality of contact pads which are uniformly spaced about the periphery thereof or by a continuous annular contact pad, the said pads or pad consisting of a low-friction material of high wear resistance.

According to the invention, each test head is provided with marking means adapted to be controlled in accordance with the result of the test and thus to render visible the flaws detected by the probes, the limits of the area of the plate to be tested and/or the origin and the direction of at least one coordinate axis.

Preferably, each plate to be tested is brought into a predetermined position in relation to the guide means, and a starting point and at least one coordinate direction are indicated on the plate by means of said marking means so as to make it possible, if the tracing pattern is known, to reconstruct those portions of the plate which were tested and the location of the flaws detected by the probes within the area traced.

The said markings may be painted onto the plate and/or produced by local magnetization of the plate and/or by suitably embossing the plate.

Thus, there has been provided by the invention a testing device of the type indicated which is easy to use, which can be suitably matched with a variety of plate products to be tested, which is capable of being constructed at a low cost, and which is particularly adapted to produce accurate test results.

Some of he objects and advantages of the invention having been stated, others will appear as the description proceeds, when taken in connection with the accompanying drawings, in which FIG. 1 is a vertical cross-sectional view of part of one embodiment of a device according to the invention;

FIG. 3 is a rear elevational view of the major part of a device according to the invention;

FIG. 3a is a foreshortened end view of the device of FIG. 3;

FIG. 4 is a vertical cross-sectional view of part of a modified embodiment of the invention;

Figure 1:
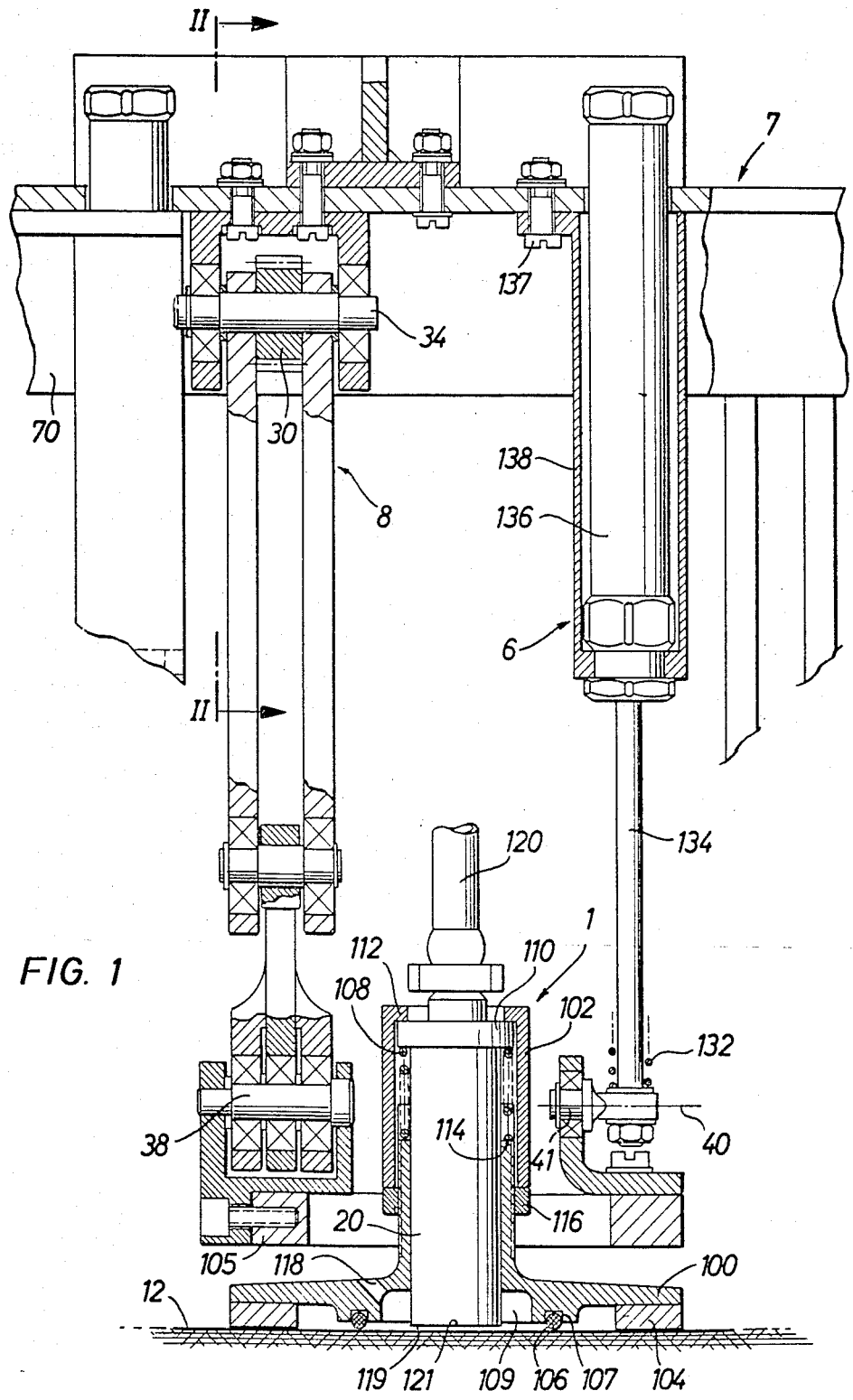

The embodiment shown in FIGS. 1 through 3b comprises five test heads, 1, 2, 3, 4 and 5 which are each provided with a test probe and which are individually connected with guide means 7 through the medium of elevating elements 6 and guide elements 8 which are capable of transmitting elevating and guiding forces in a substantially independent manner, the said test heads being laterally spaced in a predetermined manner and adapted to be recirpocated at right angles to a stationary plate surface 12 and to be positively guided in a given tracing direction.

There is associated with each of the five test heads an elevating element 6 in the form of a cylinder-and-piston unit of variable length, the cylinder member 136 of such elevating element being supported by a supporting arm 70 constituting a common support for the test heads, the rod-shaped piston member 134 of said elevating element extending from said cylinder 136 being coupled to the associated test head, each elevating element being adapted to raise the respective test head resting under its own weight on the surface 12 of the plate under test as soon as the test head assumes a position externally of the area to be tested. The cylinder member 136 is supported by a socket member 138 which is attached to said supporting arm 70 by means of bolts 137. The said piston member 134 is coupled to said test head through a pivot pin 41 mounted in a supporting ring 105 surrounding the lower portion of the test head and being separated therefrom by a predetermined radial distance, the test head being pivotally mounted in said supporting ring by means of two bearings 43 and 45 shown in FIG. 2.

Each elevating element 6 is preferably constructed in the form of a single-acting pneumatic or hydraulic cylinder.

Since it is possible in certain cases that the dead weight of each of the test heads 1, 2, 3, 4 and 5 and thus the contact pressure between each test head and the surface 12 of the plate under test becomes very great, it is possible, for the purpose of reducing dynamic friction, to operate the elevating element or cylinder-and-piston unit 6 in its elevating direction in such a manner as to compensate for the part of the weight of the test head so as to cause the test head to exert on the plate surface 12 a predetermined force which is smaller than the force which would correspond to the dead weight of the test head. It is also contemplated, according to the invention, to provide counterweights (not shown) or balancing springs (not shown) for the purpose of compensating for part of the weight of the test heads.

Preferably, the said elevating elements 6 are constructed as double-acting pneumatic or hydraulic cylinders so as to permit the test heads to be brought into contact with the plate surface 12 and to cause them to exert a predetermined force on the plate surface. This is necessary in such cases, in particular, in which the dead weight of the test heads would not suffice to move them from their raised positions into contact with the plate surface and to maintain them in contact therewith without an additional force being applied to the test heads.

Preferably, there may be provided as elevating elements between the supporting arm 70 on the one hand the test heads on the other, suitable return springs (not shown), there being additionally associated with each test head a pressure cylinder (not shown) adapted to maintain the test head in contact with the plate surface 12 in opposition to the pulling force of the return spring. Such an arrangement would afford the advantage that in the event the pressure fluid supply to the pressure cylinder should fail each test head would be automatically raised and thus be removed from the zone in front of the plate edges during the advancement of the test heads towards the next plate to be tested, the test heads thus being protected from possible damage.

As will be seen in FIG. 1, a shock absorbing spring 132 surrounds that portion of the piston member 134 which extends from the cylinder member 136, such spring serving to prevent the test elements of the test head from violently striking the cylinder member 136 upon being raised into their uppermost position.

Figure 2:
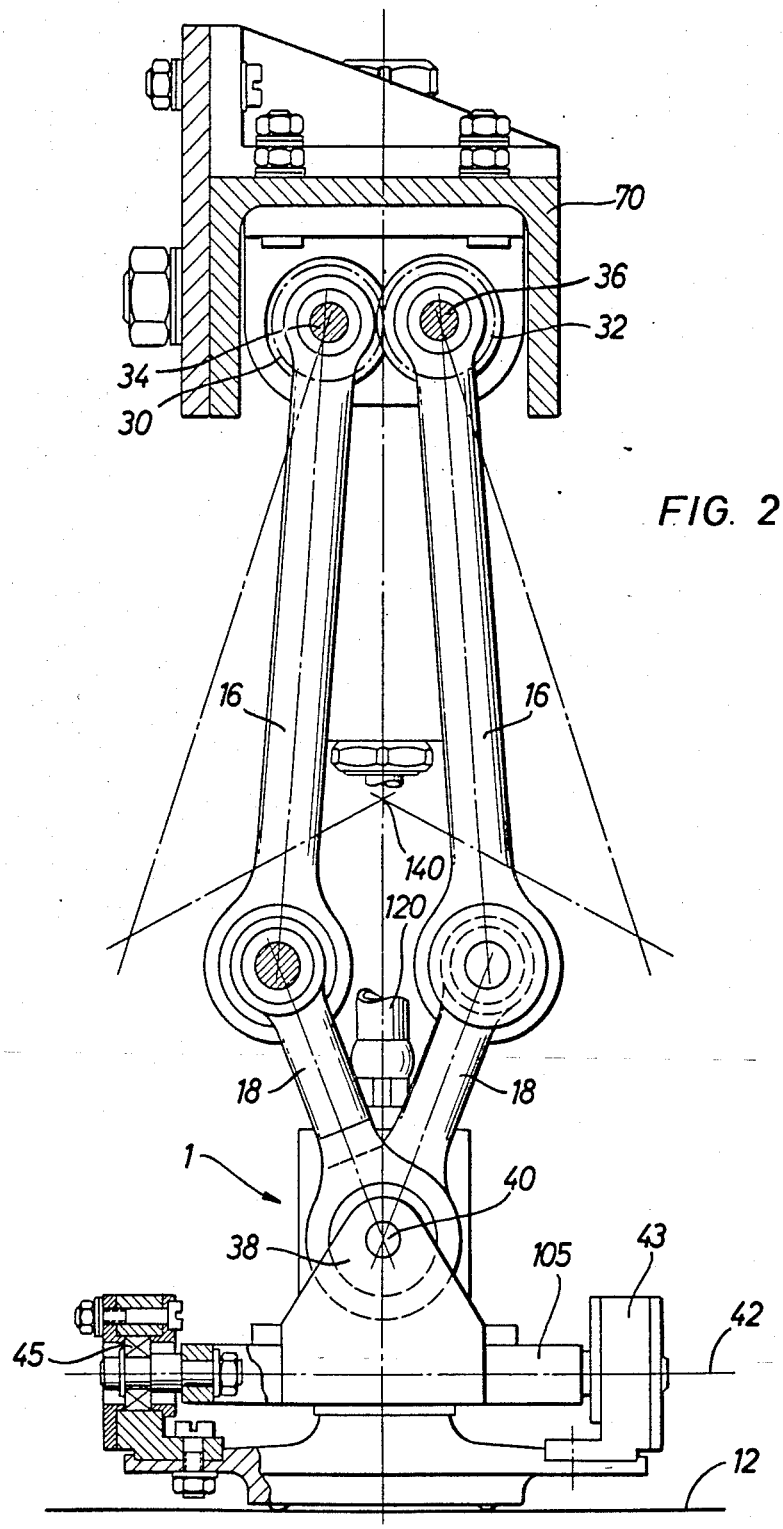
FIG. 2 is a vertical cross-sectional view on the line II—II of FIG. 1.

The guiding forces to be applied to the test heads 1, 2, 3, 4 and 5 from supporting arm 70 are primarily transmitted by the guide members 8 of which, according to FIG. 1, the upper ends are pivoted to supporting arm 70, whereas their lower ends are pivoted to the respective test head. As seen in FIG. 2, the said guide members 8 are each constructed as a toggle lever arrangement, the two upper struts 16 of each pair of toggle lever arrangements being interconnected by two interengaging gear wheels 30 and 32 in order to ensure an accurately defined deflection of said struts 16 in opposite directions.

The uppermost position 140 of pivot axis 40 in FIG. 2 is primarily determined by the length of the struts 16 and 18 of the said toggle lever arrangements and by the available length of stroke of the elevating elements 6 which preferably amounts to approximately 60 mm (2.4 inches) to 100 mm (4 inches).

Positive guidance of the test heads 1, 2, 3, 4 and 5 in the desired tracing direction is provided for by the fact that the oppositely deflectable upper struts 16 of the two toggle lever arrangements 8 are coupled to supporting arm 70 through pivotal joints 34 and 36 and that the oppositely deflectable lower struts 18 are coupled to the test head through a pivotal joint 38 as shown in FIG. 2, the arrangement being such that the rotational axes of said pivotal joints extend substantially at right angles to the direction of travel of the test heads and substantially parallel to the plate surface 12.

As will be seen in FIG. 1, the pivotal joints 38 and 41 are mounted on the upper portion of the supporting ring 105 surrounding the test head near its lower end with a predetermined radial spacing therebetween at such an elevation that the rotational axes of such joints coincide and thus constitute a first pivot axis 40 extending substantially at right angles to the direction of travel and substantially parallel to the plate surface 12, the test head being pivotable about axis 40. As will be seen in FIG. 2, the test head proper is coupled to supporting ring 105 through two diametrically oppositely arranged pivotal joints 43 and 45, the rotational axis determined by such joints extending substantially parallel to the tracing direction and substantially parallel to the plate surface 12, and said axis forming a second pivoting or tilting axis 42 which is located at a somewhat lower level than said first pivot or tilting axis 40, the test head thus being tiltable also about said second axis 42.

The gimbal suspension just described enables the associated test head to be maintained in substantially continuous contact with plate surface 12 regardless of surface irregularities, particularly wavy portions thereof.

The radial clearance between each test head and its associated supporting ring 105 is selected in such a manner as to enable the test head to perform any tilting motion caused by the surface irregularities of the plate surface 12.

The guide means 7 comprises a wheeled truss-like supporting structure 80 shown in FIG. 3 which is adapted to be traversed along a testing station 14 intended to receive the plates to be tested, said supporting structure comprising a transverse beam 82 extending at right angles to the direction of travel of the supporting structure over the entire testing station 14 and forming a guide rail for a wheeled carriage 60 supporting the test heads 1, 2, 3, 4 and 5; said transverse beam is supported by three uprights 84, 87 and 88 respectively carrying at their lower ends one of three wheels 94, 96, 98, the two wheels 94 and 96 being spaced apart along a guide rail 92 extending the length of testing station 14. Said guide rail 92 thus determines the direction of travel of supporting structure 80 and thus a first direction of travel of the test heads in relation to the plate under test.

The drive means of said supporting structure 80 may preferably comprise an endless chain 93 fixedly attached to the supporting structure and adapted to be driven by an electric motor 91 disposed in a stationary position externally of the supporting structure. It is also contemplated, according to the invention, to arrange the electric motor driving the supporting structure on such structure and to provide power transmission means adapted to cooperate with at least one of said wheels 94, 96 and 98. In the case of smaller embodiments of the invention, the supporting structure may be adapted to be moved manually by the operators thereof.

The carriage 60 which is adapted to be traversed along the transverse beam 82 at right angles to the direction of travel of the supporting structure may be secured both ends of the carriage to an endless chain 52 by means of hooks 54 and 56 as shown in FIG. 3, said chain being adapted to be operated by means of a hand crank mechanism or preferably by means of an electric motor 50.

The direction in which said transverse beam 82 extends determines a second direction of travel of the test heads 1, 2, 3, 4 and 5 supported by carriage 60 which is movable along the transverse beam.

The drive means 50 and 91 may be constructed as electrically operable stepping or servo motors permitting recording of the distances respectively travelled by supporting structure 80 along guide rail 92 and by carriage 60 along transverse beam 82.

In the embodiment of FIGS. 1 to 3b, the test heads 1, 2, 3, 4 and 5 are disposed in side-by-side relationship along a common line and are connected to carriage 60 by means of supporting arm 70 which is adapted to be pivoted about an axis 62 (FIG. 3) extending perpendicularly to plate surface 12, said supporting arm extending substantially parallel to plate surface 12, the test heads being individually suspended from said supporting arm and disposed in such a manner that the distance between mutually adjacent test heads amounts to between eight and twelve times the tracing width determined by the probes contained in the test heads, such distances being preferably about 100 mm (4 inches). This arrangement permits rapid line-by-line tracing of the surface area to be inspected, the test heads being preferably moved over the plate surface along preprogrammed paths. Preferably, the supporting arm 70 carrying the test heads 1, 2, 3, 4 and 5, after having been traversed over the plate surface, is advanced transversely of the strip-like portions just traced by an amount corresponding to 1, 2, 3 or more times the width of the said strip-like portions, the plate surface then being traced in a direction opposite to the first tracing direction. This method may be employed continuously until there remain no untraced portions between the portions or areas traced.

However, it may also be convenient to trace the areas to be checked in accordance with a grid-like pattern, this being done by pivoting the supporting arm 70 at suitable intervals by 90 degrees about a vertical axis and by then tracing the plate surface at right angles to the strip-like portions traced previously.

The supporting arm 70 is connected with the carriage 60 by means of a supporting tube assembly 66 comprising two separable tubular members 68 and 69, of which the upper member 68 is supported for rotation about its longitudinal axis by a bearing 64 attached to the underside of the carriage 60, whereas the lower member 69 is rigidly attached to supporting arm 70. Preferably, the bottom of carriage 60 is provided with locking means (not shown) adapted to cooperate with the supporting tube assembly 66, permitting the supporting arm 70 to be pivoted through a predetermined angle about a vertical axis, and further adapted, up to the time at which it is released, to retain the supporting arm 70 in the desired angular position in relation to the tracing direction of the test heads respectively determined by the directions of travel of the supporting structure 80 and of the carriage 60. The said locking means may comprise, for example, a pin which is adapted to be forced against the upper member 68 of the supporting tube assembly 66, such pin being associated with a single-acting hydraulic or pneumatic pressure cylinder which is operable to force said pin against the periphery of said upper member 68 for the purpose of locking the supporting tube assembly and thus the supporting arm 70 in its desired or predetermined angular position. Relieving the said pressure cylinder of fluid pressure will release said pin, whereupon the supporting arm may again by pivoted through any desired angle about the pivot axis determined by the supporting tube assembly 66. Preferably, the supporting arm 70 is always pivoted in such a manner that its longitudinal axis extends substantially at right angles to the direction of travel of supporting structure 80 or of carriage 60, respectively, i.e. at right angles to the tracing direction of the test heads. The said locking means may alternatively comprise a pin which is biased towards the periphery of the upper member 66 of the supporting tube assembly 66 by a compression spring and which is adapted, when it is desired to pivot the supporting arm, to be withdrawn against the bias of said spring by means of a hydraulic or pneumatic cylinder.

In the event that the supporting arm 70 does not extend at right angles to the tracing direction of the test heads 1, 2, 3, 4 and 5, the lateral distances between the strip-like portions traced by the probes 20, 22, 24, 26 and 28 carried by the test heads and thus the widths of the portions not swept by such probes will be smaller than they would be if the supporting arm 70 extended at right angles to the tracing direction of the test heads.

Thus it is possible depending on the angular position of the supporting arm 70 selected in relation to the tracing direction of the test heads as determined by the directions of travel of the supporting structure 80 and the carriage 60, selectively to perform a rough test or a precision test, the coarsest test being obtained with the supporting arm 70 extending at right angles to the direction of travel of the test heads.

Preferably, the supporting tube 66 comprises two separable parts so as to permit various testing units each comprising a supporting arm and a set of test heads to be used interchangeably. Such an interchange of testing units will be necessary in such cases, in particular, in which the plates to be tested are of such thickness as to require test probes of different capacity.

Preferably, the lower member 69 of the supporting tube assembly 66 which is rigidly attached to the supporting arm 70 is insertable from below into the upper member 68 which is rotatably supported from the bottom of carriage 60 and is adapted to be locked in position by means of clamping elements not shown. This arrangement will permit the elevation of the supporting arm above the plate surface 12 to be adjusted and maintained, such elevation being selected in such a manner as to permit the test heads to follow all surface irregularities of the plate surface and to be maintained in constant contact therewith.

In order to permit the test heads to be locked in any desired position in relation to the plate surface, for example at the location of a strong ultrasonic echo indicating the presence of a defect, both the supporting structure 80 and the carriage 60 may be provided with brake means not shown.

Preferably, such locking brakes comprise shoe-type brakes cooperating either with said wheels 94, 96, 98 or directly with said guide rails 82 and 92 and operable by means of single-acting hydraulic or pneumatic pressure cylinders.

Figure 5:
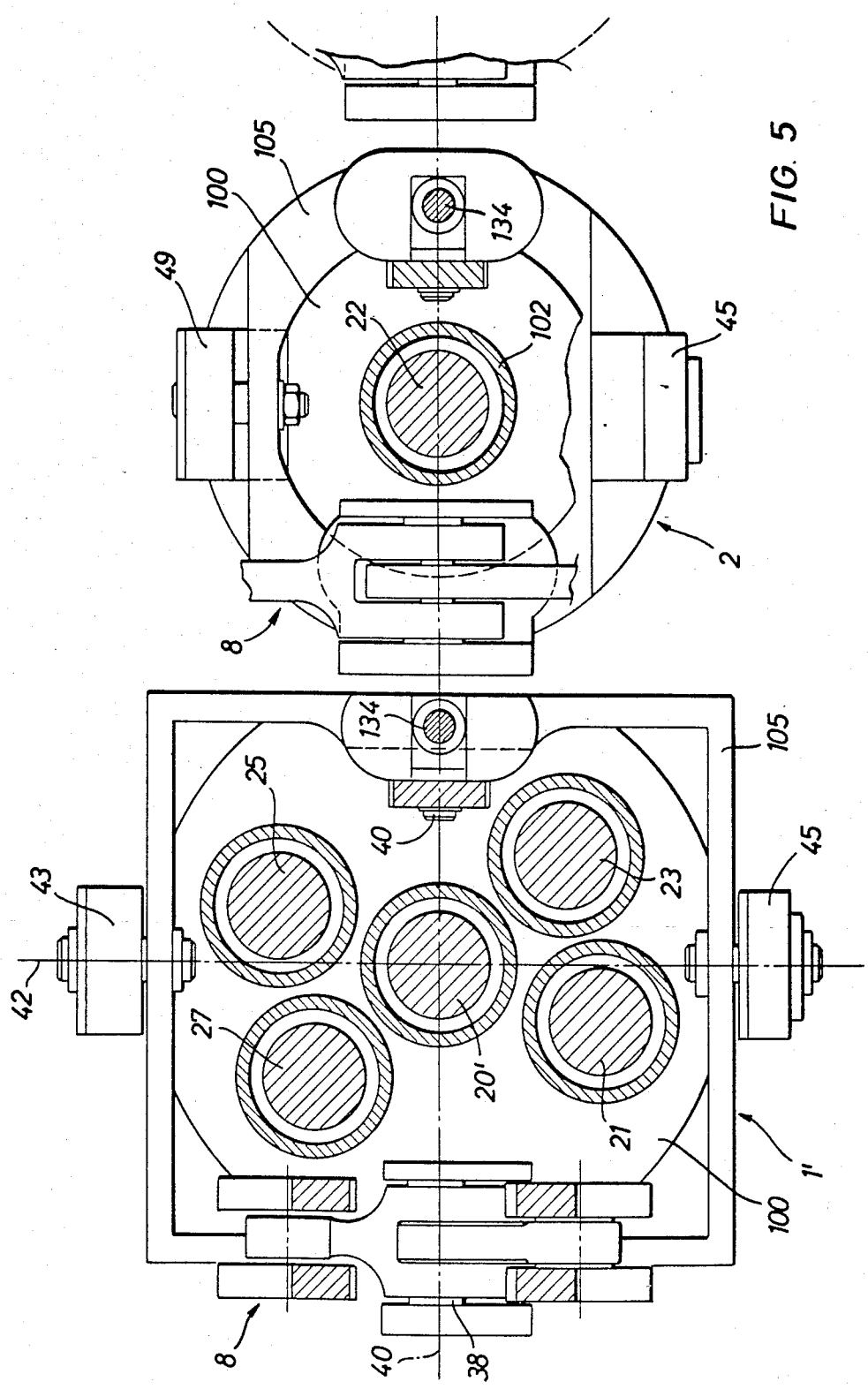
FIG. 5 is a cross-sectional view of the broken line V—V of FIG. 4.

Each of the test heads 1, 2, 3, 4 and 5 houses a plurality of test probes 20, 22, 24, 26 and 28 each of which preferably comprises a probe of conventional construction including an ultrasonic transmitter and and ultrasonic receiver operating on the pulse transit time principle, such probes, as shown in FIG. 5, being mounted in a common probe holder 100 for vertical reciprocation relative to the plate surface 12. As shown in FIG. 5, a compression spring 108 bearing on the upper end face 114 of probe holder 100 and an annular shoulder 110 provided on the upper end of the probe serves to urge each probe against the under surface 112 of a radially inwardly projecting flange formed on a substantially cylindrical socket 102 which is in screw-threaded engagement with the probe holder, the said screw-threaded engagement enabling selective adjustment of each probe within probe holder 100 in a longitudinal direction for the purpose of adjusting the width of the gaps 119 between the ultrasound transmission and receiving surfaces 121 of the probes on the one hand and the plate surface 12 on the other, the width of such gaps influencing the transmission of ultrasonic energy. According to FIG. 1, an annular lock nut 116 screwed onto the stem of probe holder 100 permits the socket 102 to be locked in relation to the probe holder in any desired vertical position.

For the purpose of permitting a coupling fluid to be introduced into the area 109 surrounding the ultrasound transmitting and receiving surface 121 of the probe, the upper surface of the probe holder 100 has formed therein a bore 118 adapted to receive a supply tube or hose not shown. Water is preferably used as coupling fluid or medium.

The area 109 is defined at its periphery by a sealing ring 106 which is preferably formed as an O-ring mounted in an annular groove 107 formed in the underside of probe holder 100 and adapted substantially to prevent the escape of coupling fluid introduced into the area 109 through the bore 118.

The probe holder 100 is adapted to bear on the plate surface 12 through the medium of a plurality of pads 104 which are preferably equiangularly spaced about the periphery thereof. Alternatively, a substantially continious annular pad may be employed. The said pads or the annular pad are preferably made of a low-frictional material of high wear resistance.

As shown in FIG. 3, there are provided a plurality of coaxial cables 120, 122, 124, 126 and 128 having the function of transmitting the original electric pulses produced by a generator not shown and transformed into ultrasonic pulses by ultrasonic transducers housed in the probes 20, 22, 24, 26 and 28 as well as the reflected ultrasonic pulses produced either by defects in the plate or by the underside of the plate and converted into electric pulses by ultrasonic receivers housed in said probes, which latter pulses have to be supplied to a recording means not shown. The flaw recording means which preferably includes an oscilloscope screen and-/or X-Y plotter is preferably located on the supporting structure 80; in the case of the smaller embodiments of the invention adapted for manual operation such recording means are preferably disposed within the field of view of the operators pushing the device. However, in the case of larger-size devices powered by electric motors, it may be convenient, where the said recording means are not movable together with the supporting structure 80, to employ stationary recording means positioned in the vicinity of the location of the personnel charged with controlling the motion of the supporting structure and/or the carriage.

Preferably, each test head is provided with a marking means, for example in the form of a paint spray gun, adapted to be operated in response to the test results and permitting the flaws detected by the probes to be rendered visible. Such marking means, particularly those marking means which are associated with the test head 1 or 1' arranged in the vicinity of the periphery of the plate under test, or a special marking means mounted on carriage 60, may be employed to mark on the plate surface the limits of the plate area to be tested or to mark the origin of the tracing pattern to be followed by the test heads. Where said origin is marked, there is preferably also marked at least one coordinate direction. Such marking means make it possible, before further processing of the plates, either to mark or subsequently to reconstruct the plate areas tested and the location of objectionable flaws detected.

Preferably, the device is further provided with control means not shown permitting the traverse motions of the supporting structure and the carriage as well as the pivotal motion of the supporting arm 70 about axis 62 to be controlled in such a manner as to cause the test heads to follow any one of a plurality of pre-programmed tracing patterns corresponding to different quality standards, the arrangement being such that it is possible to record and preferably to store on a suitable data carrier information on the location of the flaws relative to a system of coordinate axes and/or their extent in space and/or their vertical position within the plate. FIGS. 4 and 5 show a second embodiment of a device according to the invention of which parts corresponding to parts of the aforedescribed embodiment of FIGS. 1 to 3b are designated by like reference numerals. To be more specific, FIGS. 4 and 5 show a modified embodiment permitting to subject to a precision test those portions of a plate 10 which, after cutting the plate to the desired final dimensions, will constitute the edge or marginal portions thereof, and to subject to a rough test those portions of the plate which are located internally of such edge or marginal portions. This problem-oriented method of tracing of the plate surface is of particular importance in view of the fact that particularly those flaws which are located in said edge or marginal portions are apt to give rise to the formation of cracks, this applying especially to cases in which welding operations have to be performed in such areas.

Figure 3B:
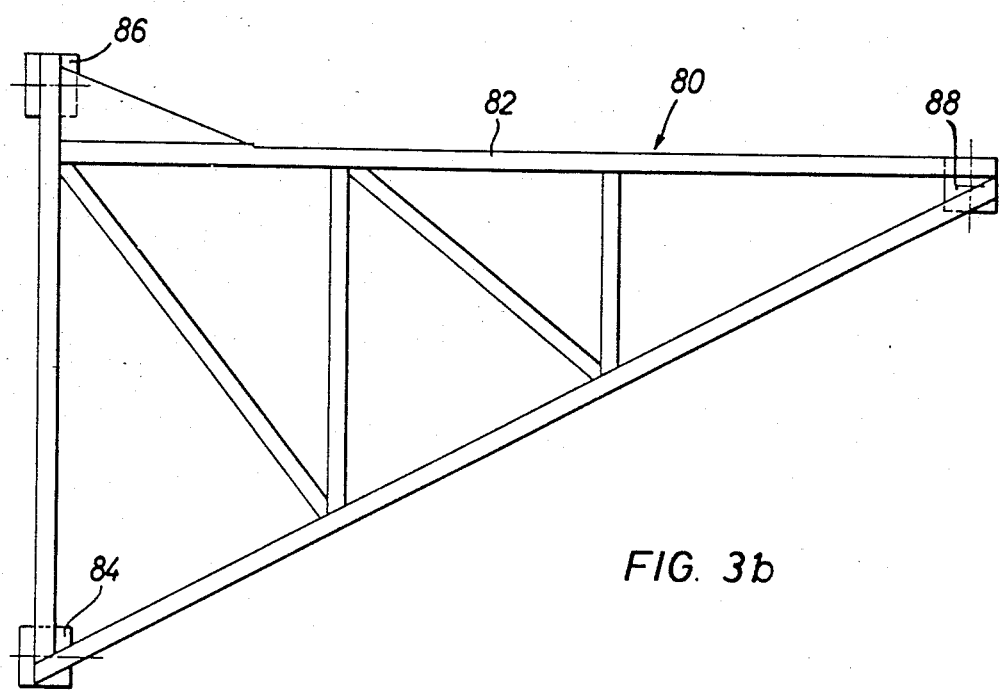
FIG. 3b is a reduced scale plan view of the device of FIG. 3.

In the embodiment of FIGS. 4 and 5, the said supporting arm 70 is provided, at the end thereof which is arranged in the vicinity of the periphery of the plate to be tested, with a test head 1' which takes the position of the test head 1 of the embodiment of FIGS. 1 to 3b and which comprises five mutually offset test probes 20', 21, 23, 25 and 27 arranged in such a manner that the distances between adjacent probes measured in a direction perpendicular to the tracing direction equal the width of the strip-like portions swept by the probes. In this manner, the probes 20', 21, 23, 25 and 27 housed in the test head 1' determine a substantially continuous strip-like portion to be traced having a width which equals five times the width of a portion swept by a single probe. The distances between the test probes 20', 22, 24, 26 and 28 housed in the test heads 1', 2, 3, 4 and 5 and arranged along a common line as shown in FIG. 3 are substantially identical and amount to between eight and twelve times the width of a strip-like portion swept by a single probe, such distances being preferably 100 mm (4 inches), the result being that it is possible, with the probes 21, 23, 25 and 27 surrounding the probe 20' having been rendered inoperative, to perform a rough test of the type described in connection with the embodiment of FIGS. 1 to 3b and, with the probes 22, 24, 26 and 28 housed in test heads 2, 3, 4 and 5 rendered inoperative, to perform a precision test using the probes 20', 21, 23, 25 and 27 housed in test head 1'.

Such a change-over from a precision test to a rough test and vice versa is required in such cases, in particular, in which the said recording means has but five input channels and in which it is normally required to perform a rough test using the device of FIGS. 1 to 3b.

However, it may prove very convenient to provide the device of the invention with recording means having nine or more input channels so as to permit the periphery of a plate to be traced for the purpose of performing a precision test in respect of the marginal areas thereof and simultaneously a rough test in respect of the areas located interiorly of said marginal areas.

Figure 6:
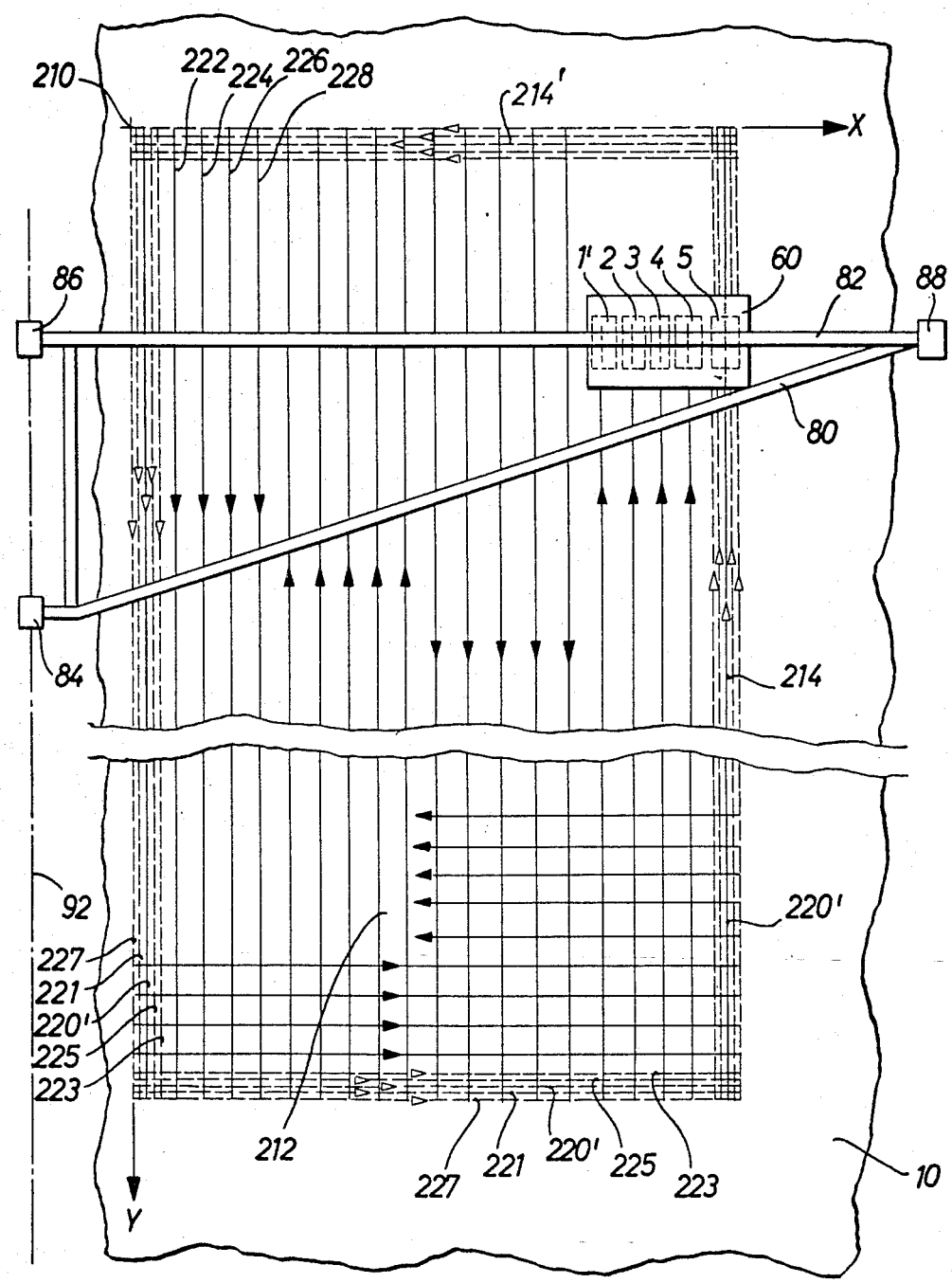
FIGS. 6 and 7 are plan views showing examples of tracing patterns.

FIG. 6 shows an example of a pattern according to which a plate 10 having predetermined width and length dimensions may be traced methodically; in this case, a predetermined rectangular surface area 212 of plate 10 is first traced by means of test heads 1', 2, 3, 4 and 5 in the direction of the arrows along the marginal portion 214 to be subjected to a precision test, i.e. along the strip-like portions 220', 221, 223, 225 and 227, whereupon the inner area which is to be subjected to a rough test is traced in the direction of the arrows along the strip-like portions 220', 222, 224, 226 and 228 with the probes 22, 24, 26 and 28 of test heads 2, 3, 4 and 5 associated with the strip-like portions 222, 224, 226 and 228 being maintained inoperative during the precision test, and with the probes 21, 23, 25 and 27 of test head 1' associated with the strip-like portions 221, 223, 225 and 227 being maintained inoperative during the rough test.

At the commencement of the test, the heads 1', 2, 3, 4 and 5 are brought into contact with the plate 10 to be tested at the upper left-hand corner of the plate shown in FIG. 6 at a point 210 constituting the origin of the tracing pattern, whereupon the test heads are first traversed along the left-hand edge of the plate through the specified distance in the direction of the Y-axis of an X-Y system of coordinates having its origin at the point 210 and encompassing said predetermined surface area 212, said test heads being guided along the strip-like portions 220', 221, 223, 225 and 227, the direction of the Y-axis being determined by the transverse beam 82 constituting a guide rail for carriage 60 and extending at right angles to guide rail 92; upon the end of the specified distance being reached, the test head assembly is pivoted through 90°, whereupon, taking as a starting point the outermost strip-like portion 227, the test head assembly is traversed transversely of the strip-like portions 220', 221, 223, 225 and 227 in the X-direction until the specified width of the plate to be tested is reached; it should be understood that, during the testing of the plate margins only the probes 20', 21, 23, 25 and 27 of testing head 1' are operative.

After the remaining marginal area 214, 214' of plate 10 has been traced, the probes 21, 23, 25 and 27 of test head 1' are disconnected, and the probes 20', 22, 24, 26 and 28 of test heads 1', 2, 3, 4 and 5 are rendered operative; next, the inner area of plate 10 which is subjected to a rough test is traced along strip-like portions 220', 222, 224, 226 and 228 also extending in the Y-direction, with the tracing motion again starting at the upper left-hand corner of the plate, it being understood that probe 20', in this example, is moved for a second time along the strip-like portion 220' at the left-hand edge of said predetermined surface area 212 in the same manner as it was moved during the precision test.

Upon the test heads 1', 2, 3, 4 and 5 having reached the lower border of the plate section having the length specified, the test heads are displaced in the X-direction towards the right by an amount corresponding to five times the distance between any two adjacent strip-like portions traced, whereupon the test heads are traversed in the opposite direction in relation to the plate. The aforedescribed steps are repeated until the entire plate area has been traced in a strip-by-strip manner. When the test heads, upon reaching the end of the tracing line, are displaced towards the right in the X-direction by an amount corresponding to five times the distance between any two adjacent strip-like portions, there will result a strip pattern in which there are identical distances between any two adjacent strip-like portions over the entire width of the surface area to be tested, such distances preferably correspond to between eight and ten times the width of a strip-like portion traced by a single probe. Preferably, the test heads are displaced by equal amounts towards the right, i.e. in the X-direction, such amounts being so selected that the strip-like portion 228 associated with probe 28 will coincide with the strip-like portion 220' traced by probe 20 of test head 1' during precision testing of the right-hand margin of the predetermined surface area 212 as shown in FIG. 6.

Turning off the probes 21, 23, 25 and 27 during a rough test and turning off the probes 22, 24, 26 and 28 during a precision test will always be necessary in cases in which use is made of flaw recording means having only five test signal inputs, one probe each being associated with each input. Where a flaw recording means having nine input channels is employed, it is possible, when the marginal area 214 is being given a precision test, simultaneously to rough-test a portion of the internal area of plate 10 which it is desired to be subjected such a rough test.

At the bottom of FIG. 6 there is shown a portion of the plate 10 to be tested, said portion having a predetermined suface area and being traced according to a grid-like pattern after the peripheral margins of the plate have been tested; it will be seen that within the marginal area 214 of plate 10 the strip-like portions traced during the rough test are superimposed to the strip-like portions traced during precision testing of the marginal areas. This system affords added safety as regards reliability in the detection of flaws possibly present in the critical marginal areas.

The distance travelled by the test heads may be measured by means of measuring means not shown which are respectively mounted on the supporting structure 80 and the carriage 60, each measuring means comprising a measuring wheel and a pulse generator associated therewith, said measuring wheels preferably being adapted to cooperate with the guide rail 92 and the transverse beam 82, respectively, the latter also constituting a guide rail, each pulse generator being adapted to supply 500 pulses per revolution of its associated measuring wheel, and the periphery of each measuring wheel having a length of 500 mm (19.685 inches); with this arrangement, 1 pulse generated corresponds to a length of travel of 1 mm (0.0394 inches).

In the above case, the distance travelled and, particularly, the location of the flaws may be measured by counting the pulses which are generated as the supporting structure 80 is traversed along the guide rail 92 extending in the Y-direction and as the carriage 60 is traversed along the transverse beam 82 extending in the X-direction, i.e. at right angle to the guide rail 92, such pulses being produced by said pulse generators which are respectively associated with the supporting structure and the carriage, the pulse counts being referred to the point of origin 210.

In order to prevent the test heads from being damaged by contact with the edges of the plate to be tested, provision is made for the outermost strip-like portion 227 traced by test head 1' to be spaced at least between 180 mm (7 inches) and 250 mm (10 inches) from the outer edges of the plate.

Figure 7:
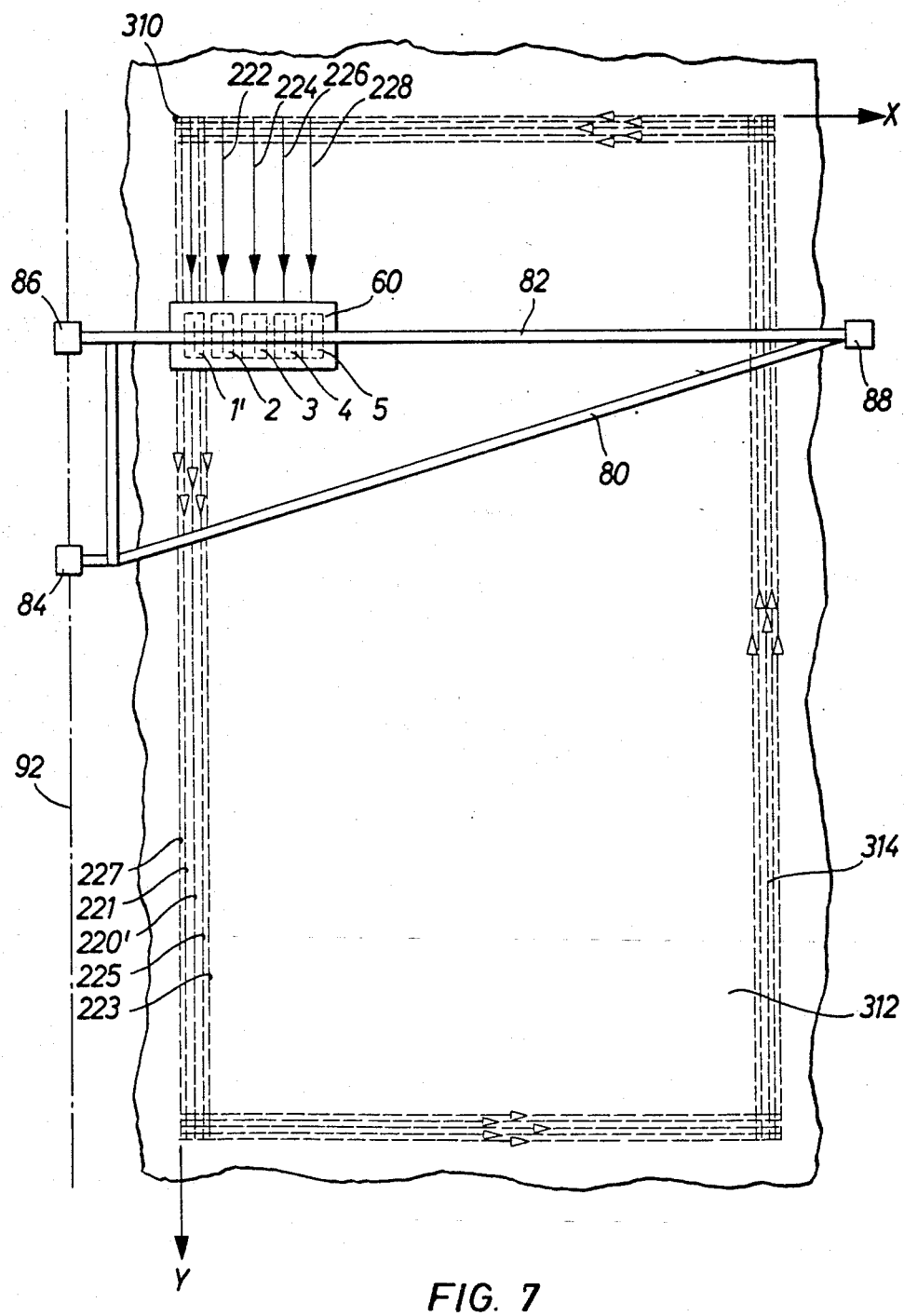

FIG. 7 shows an example of a method of systematically tracing a plate 10 the outside dimensions of which are substantially determined by the as-rolled size of the plate rather than by predetermined dimensions as specified by the customer. In FIG. 7 all parts which have been retained unchanged are designated by similar reference numerals as in FIG. 6. The plate 10 of FIG. 7 is traced according to a pattern which resembles that employed in FIG. 6, i.e. the peripheral portions 314 of the plate are generally subjected to a precision test, whereas the inner area 312 surrounded by said peripheral portions is to be subjected to a rough test. In view of the fact that the edges of plate 10 are frequently very irregular and that it is necessary positively to prevent the outermost test head from being damaged by such irregular edges, there must be maintained a minimum distance of about 180 mm (7 inches) to 250 mm (10 inches) between the outermost test head and the plate edge.

Furthermore, in order to prevent the test heads from being damaged as they are advanced towards an edge of the plate, the testing device is provided with suitable feelers (not shown) adapted to control elevating and/or lowering motions of the test heads.

Preferably, there are associated with each test head at least two mechanically deflectable feeler rods, each feeler rod being connected to an electric switch, a first feeler rod being arranged, with reference to the direction of travel, in front of each test head, and a second feeler rod being arranged to the rear or each test head.

As the test heads 1',2, 3, 4 and 5 are advanced towards one edge of the plate, and before the test heads arrive at one edge, the two feeler rods are in their non-deflected home positions, the test heads being in their uppermost positions in which they are held, for example, by the elevating cylinder 136 shown in FIG. 1, the elevation of the test heads being sufficient to prevent the test heads from coming into contact with a plate edge or the plate surface during their advancement towards the edge and during the tracing operation, respectively.

Upon the plate edge in question being reached, the first said feeler rod will be deflected by such edge, the test heads still being retained in their elevated positions. After the second feeler rod has been deflected by the plate edge, the test heads are lowered onto the plate surface and then maintained in contact therewith until the first feeler rod, after leaving the plate edge at the opposite end of the plate, has returned into its home or rest position. Upon the first feeler rod leaving said plate edge and returning to its inoperative position, the test heads are again elevated.

The arrangement just described ensures that the test head will not drop beyond the plate edge upon leaving the plate surface. Besides that, the said feeler rods controlling the elevating and lowering motions of the test heads will positively prevent the test heads from striking a plate edge as they are advanced towards an edge of the plate to be tested.

Alternatively, there may be provided, as a feeler element, a helical spring which is rigidly connected to the actuating pin of an electric switch.

It is also possible to substitute for mechanically deflectable feelers feeler means adapted to respond to optical or acoustic signals. Where such feeler and control means for the elevating and lowering motions of the test heads are employed, each plate is preferably first traced in one direction, such as the Y-direction, along strip-like portions, whereupon strip-like portions are traced which extend in a second direction, i.e. the X-direction which extends at right angles to the Y-direction so that a grid-like tracing pattern is obtained.

Where feelers of the aforementioned type are employed, the device of the invention may be operated as a fully automatic testing device.

It is possible, with the device of the invention, to employ substantially any other desired tracing pattern including, for example, zig-zag patterns, meander-shaped patterns and the like.

It is also possible, in connection with such different tracing patterns, for the purpose of locating flaws, to emloy measuring means comprising a measuring wheel and a pulse generator, such measuring means being of the type aforeindicated and being respectively mounted on said supporting structure 80 and said carriage 60, such measuring means enabling the distances travelled by the test heads to be determined with reference to a preselected origin 310 and a pair of normally mutually perpendicular X- and Y-axes, the Y-axis of FIG. 7, in similarity to the arrangement of FIG. 6, again being determined by the guide rail 92, and the X-axis again being determined by the transverse beam 82 supporting the carrige 60 traversable therealong and extending at right angles to guide rail 92.

Where the supporting structure and the carriage 60 are driven by electrically operable stepping or servo motors, the location of flaws in the plate under test may be determined with the aid of such motors which are adapted to record the distances travelled by supporting structure 80 and carriage 60 along guide rail 92 and transverse beam 82, respectively.

In the drawings and in the specification, there have been set forth preferred embodiments of the invention and, although specific terms are employed, they are used in a generic and descriptive sense only and not for the purposes of limitation, the scope of the invention being defined in the claims.

What I claim is:

1. A device for the non-destructive testing of rolled steel plate and the like for the presence of internal flaws or defects, such as non-metallic inclusions, inhomogeneities and the like, comprising a carriage adapted to be traversed in relation to the surface of the plate to be tested and parallel thereto, said carriage having attached thereto, through the medium of connecting links, at least one ultrasonic test head including an ultrasonic transmitter and an ultrasonic receiver supported by a test head holder and adapted to be tilted about two mutually perpendicular tilting axes extending substantially parallel to the surface of the plate to be tested, the said connecting links comprising a number of elevating means the number of which corresponds to the number of test head holders present, each said elevating means cooperating with one of said test head holders, said elevating means being adapted individually to raise and lower said test head holders at right angles to said plate surface, characterized in that said connecting links associated with each test head holder comprise both an elevating cylinder and a separate guide means adapted positively to guide said test head holder in a direction extending at right angles to the raising and lowering direction, said guide means including two pairs of toggle lever means having first strut means proximal to said carriage and provided with toothed portions adapted to ensure positive symmetrical deflection of said first strut means in relation to the raising and lowering direction of said test head holders, and second strut means proximal to said test head holder, said second strut means and said elevating cylinder being coupled to said test head holder through pivotal joints having a common rotational axis constituting one of said two tilting axes of said test head holder.

2. A device according to claim 1, characterized in that each test head comprises at least one test probe.

3. A device according to claim 2, characterized in that said test probes each of which comprises an ultrasonic transmitter and an ultrasonic receiver are adjustably mounted within a probe holder.

4. A device according to claim 3, characterized in that each probe holder is formed on its upper side with a bore adapted to introduce a coupling medium into the area surrounding the ultrasound transmitting and receiving surface of said test probe.

5. A device according to claim 2, characterized in that said test heads are arranged on one end of said supporting arm in such a way that the distances between the strip-like portions of the plate surface traced by mutually adjacent test heads are substantially equal to the width of the strip-like portion traced by one test probe, and that the remaining test heads are arranged on said supporting arm in such a way that the distances between the strip-like portions traced by mutually adjacent test heads are equal to an integral multiple of the strip-like portion traced by a test probe.

6. A device according to claim 1, characterized in that at least one test head comprises two or more test probes which are spaced apart by distances equaling the width of the strip-like portion of said plate surface traced by each test probe.

7. A device according to claim 1, characterized in that said test head holder is adapted to bear against said plate surface through the medium of a plurality of bearing pads which are uniformly spaced along the periphery of said test head and/or through the medium of a bearing ring, and that said test head holder is preferably sealed along its periphery by means of a sealing ring.

8. A device according to claim 1, characterized in that said carriage is supported by a supporting structure which is adapted to be traversed along a testing station adapted to receive a plate to be tested, and that said supporting structure comprises at least one transverse beam extending at right angles to the traversing direction of said supporting structure and substantially over the entire area of the plate surface to be tested, said transverse beam being formed as a guide rail or track adapted to cooperate with wheels adapted to support said carriage.

9. A device according to claim 8, characterized in that said supporting structure comprises three wheels of which at least two wheels which are spaced apart in the direction of travel of said supporting structure are in guidable engagement with a guide rail extending along said testing station.

10. A device according to claim 9, characterized in that said device comprises first drive means adapted to traverse said supporting structure along said guide rail, and second drive means adapted to traverse said carriage along said transverse beam.

11. A device according to claim 10, characterized in that said drive means adapted to traverse said supporting structure and said carriage, respectively, comprise electric motors.

12. A device according to claim 10, characterized in that said drive means adapted to traverse said supporting structure and said carriage are constructed as stepping or servo motors adapted to record the distances travelled by said supporting structure along said guide rail and the distances travelled by said carriage along said transverse beam.

13. A device according to claim 9, characterized in that said supporting structure is adapted to be locked in position in relation to said guide rail through the medium of locking means mounted in said supporting structure and adapted to cooperate with the wheels carrying said supporting structure or with the said guide rail.

14. A device according to claim 8, characterized in that said carriage is adapted to be locked in position in relation to said transverse beam through the medium of brake means mounted on said carriage and adapted to cooperate with the wheels of said carriage or with said transverse beam which forms a guide track for said carriage.

15. A device according to claim 1, characterized in that each test head comprises marking means adapted to be controlled in response to the result of the test and adapted to render visible the defects detected by the probes associated therewith.

16. A device according to claim 15, characterized in that said carriage or that test head which is disposed adajcent to the periphery of said plate to be tested comprises marking means adapted to mark on said plate surface a reference point or the limits of the area of the plate surface which has been tested.

17. A device for the non-destructive testing of rolled steel plate and the like for the presence of internal flaws or defects, such as non-metallic inclusions, inhomogeneities and the like, comprising a carriage adapted to be traversed in relation to the surface of the plate to be tested and parallel thereto, and said carriage having attached thereto, through the medium of connecting links, at least one ultrasonic test head including an ultrasonic transmitter and an ultrasonic receiver supported by a test head holder and adapted to be tilted about two mutually perpendicular tilting axes extending substantially parallel to the surface of the plate to be tested, the said connecting links comprising a number of elevating means the number of which corresponds to the number of test head holders present, each said elevating means cooperating with one of said test head holders, said elevating means being adapted individually to raise and lower said test head holders at right angles to said plate surface, characterized in that said connecting links associated with each test head holder comprise both an elevating cylinder and a separate guide means adapted positively to guide said test head holder in a direction extending at right angles to the raising and lowering direction, and that said elevating cylinder and said guide means are coupled to said test holder through the medium of pivotal joints having a common rotational axis constituting one of said two tilting axes of said test head holder, and in that said connecting links comprise a supporting arm coupled to said carriage, extending substantially parallel to said plate surface and adapted to be pivoted about a pivot axis extending substantially perpendicular to said plate surface, a plurality of said test head holders being coupled to said supporting arm through the medium of one elevating cylinder and one guide means.

18. A device according to claim 17, characterized in that said supporting arm is adapted to be vertically adjusted in relation to said plate surface.

19. A device according to claim 17, characterized in that said supporting arm is adapted to be set at different angles in relation to the direction of travel of said carriage and to be locked in any given angular position.

20. A device according to claim 17, characterized in that said supporting arm is connected to said carriage through the medium of a supporting tube assembly comprising two separable members and extending at right angles to said plate surface, that the said two members of said supporting tube assembly are telescopically slidable in relation to each other, that said members are adapted to be locked together through the medium of clamping elements, that the upper member of said supporting tube assembly is supported for rotation in a bearing provided on the underside of said carriage and that the lower member of said supporting tube assembly is rigidly attached to said supporting arm.

21. A device according to claim 20, characterized in that said bearing pads or said bearing ring respectively consist or consists of a low-friction material of high wear resistance.

22. A device according to claim 17, characterized in that said supporting arm is detachably coupled to said carriage.

23. A device for the non-destructive testing of rolled steel plate and the like for the presence of internal flaws or defects, such as non-metallic inclusions, inhomogeneities and the like, comprising a carriage adapted to be traversed in relation to the surface of the plate to be tested and parallel thereto, said carriage having attached thereto, through the medium of connecting links, at least one ultrasonic test head including an ultrasonic transmitter and an ultrasonic receiver supported by a test head holder and adapted to be tilted about two mutually perpendicular tilting axes extending substantially parallel to the surface of the plate to be tested, the said connecting links comprising a number of elevating means the number of which corresponds to the number of test head holders present, each said elevating means cooperating with one of said test head holders, said elevating means being adapted individually to raise and lower said test head holders at right angles to said plate surface, characterized in that said connecting links associated with each test head holder comprise both an elevating cylinder and a separate guide means adapted positively to guide said test head holder in a direction extending at right angles to the raising and lowering direction, and that said elevating cylinder and said guide means are coupled to said test head holder through the medium of pivotal joints having a common rotational axis constituting one of said two tilting axes of said test holder, in that each test head comprises at least one test probe, each test probe having an ultrasonic transmitter and an ultrasonic receiver adjustably mounted within a probe holder, and in that each test probe is urged against an internal surface of an annular flange formed on a cylindrical socket which socket is in screw-threaded engagement with said probe holder through the medium of spring bearing with one end thereof against an upper end face of said probe holder and with the other end thereof against an annular projection formed on the upper end of said probe, and that each test probe is adapted to be axially displaced within the probe holder by screwing said socket in relation to said probe holder.

* * * * *